Sept. 6, 1966 H. C. SWIM Plant Pat. 2,668
CAMELLIA PLANT
Filed Sept. 22, 1965
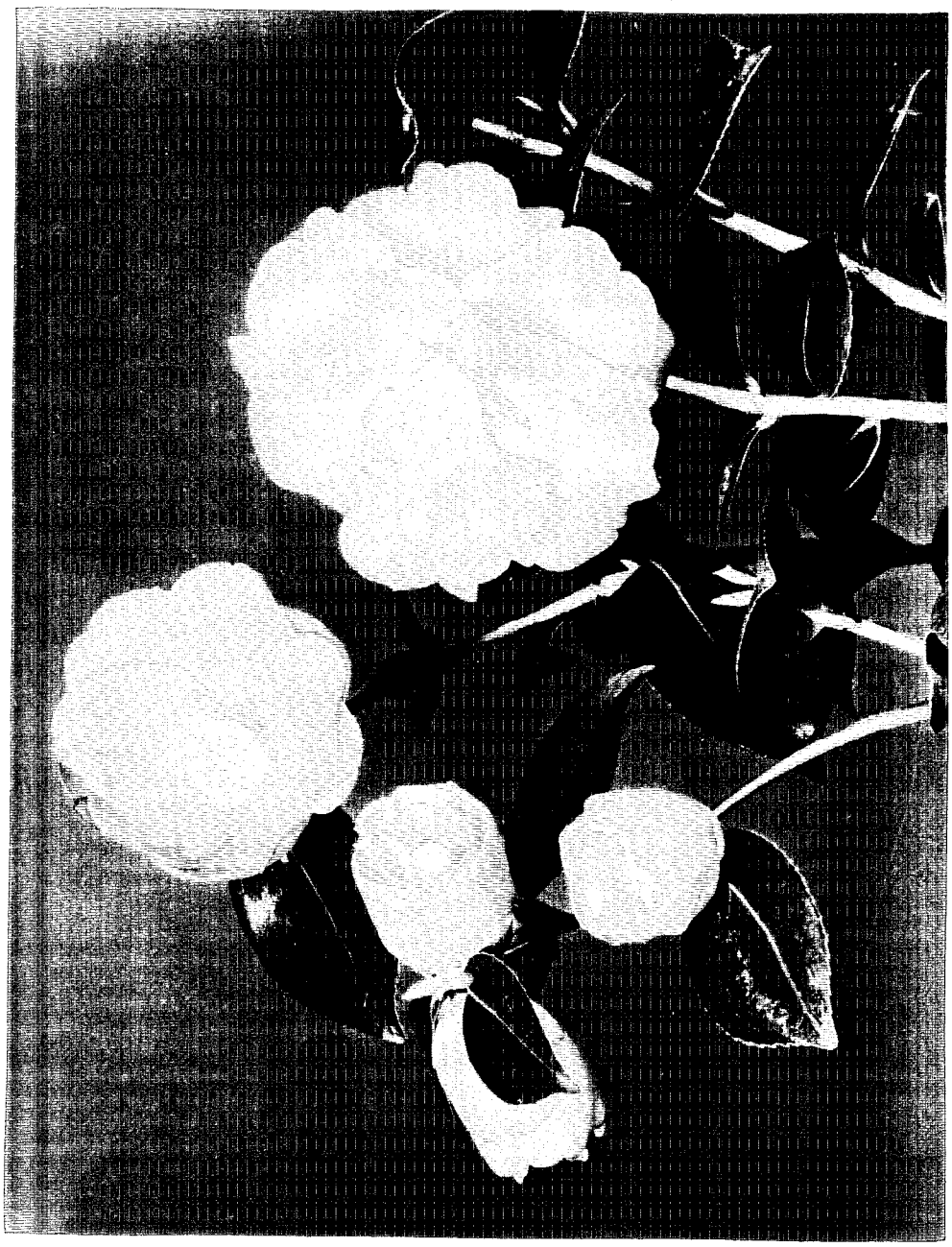
Inventor.
H. C. Swim
By: Robb & Robb
Attorneys.

United States Patent Office

Plant Pat. 2,668
Patented Sept. 6, 1966

2,668
CAMELLIA PLANT

Herbert C. Swim, Ontario, Calif., assignor to Armstrong Nurseries, Inc., Ontario, Calif., a corporation of California Filed Sept. 22, 1965, Ser. No. 489,447
1 Claim. (Cl. Plt.—62)

The present invention relates to a new and distinct variety of camellia plant which was originated by me by crossing the variety of *Camellia japonica* known as "Ville de Nantes" (unpatented) with the variety of *Camellia xwilliamsii* known as "J. C. Williams" (unpatented), the former being the seed parent and the latter being the pollen parent.

The general objective of this breeding was to produce a new and improved camellia variety in which there is combined the red flower color, large flower size, greater flower petalage and bushier plant habit of the parent variety "Ville de Nantes" with the greater floriferousness and precocious flowering habit of the parent variety "J. C. Williams." This objective was fully achieved, along with other desirable improvements, as evidenced by the unique combination of the following characteristics which are outstanding in the new variety and which distinguish it from its parents, as well as from all other varieties of which I am aware:

(1) A moderately vigorous, upright-spreading and bushy plant habit;

(2) Attractive, medium-sized, dark green, leathery and glossy foliage;

(3) A precocious flowering habit, with the flowers blooming well while the plant is still quite small and young, as compared with other *C. japonica* varieties;

(4) A very floriferous habit, with the flowers borne both terminally and laterally on the stems;

(5) Attractive, semi-double flowers of graceful, irregular form;

(6) A distinctive, attractive and bright general color tonality of the flowers corresponding to near Currant Red, with a glowing quality that is characteristic of *C. japonica* and *C. saluenensis* hybrids;

(7) A mid-season to late blooming period; and (8) A habit of all flowers dropping cleanly as one flower.

In comparison with its seed parent, "Ville de Nantes," my new variety is more precocious in flowering habit; the margins of the flower petals are generally entire, with only one or two notches, instead of the usual fimbriated petal margins of the flowers of this parent; the near Currant Red flower color is lighter than the dark red flower color of this parent; and the plants essentially set no seed pods instead of setting a great many seed pods usually set by "Ville de Nantes."

As compared with its pollen parent, "J. C. Williams," the new variety bears semi-double flowers, while the flowers of this parent are single; and the flower color is near Currant Red, while that of the parent variety is Phlox Pink.

Asexual reproduction of my new variety by both grafting and by cuttings, as performed at Ontario, California shows that the foregoing characteristics and distinctions come true and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W) and Robert Ridgway's color Standards and Nomenclature (hereinafter abbreviated as (R)), as indicated:

Type: Ornamental; flowering evergreen shrub; for general landscape use and for cut flowers.

Class: *Camellia japonica* type.

Breeding: Seedling.

*Seed parent.*—"Ville de Nantes."

*Pollen parent.*—"J. C. Williams."

Propagation: Holds its distinguishing characteristics through succeeding propagations by both grafting and cuttings.

*Plant*

Growth:

*Habit.*—Upright-spreading; moderately branched; somewhat open.

*Vigor.*—Medium.

*New stems.*—Medium caliper; glabrous. Color—near Absinthe Green, Plate XXXI (R).

*Older stems.*—Glabrous, becoming fissured and scurfy. Color—between Russet, Plate XV (R) and Cinnamon-Brown, Plate XV (R).

*Mature branches.*—Rough and scurfy when a year or two old, becoming more smooth as original bark is sloughed off. Color—between Drab-Gray, Plate XLVI (R) and Light Grayish-Olive, Plate XLVI (R).

Leaves:

*Habit.*—Moderately abundant.

*Texture.*—Leathery.

*Size.*—Medium; from 4½ cm. to 5 cm. wide; from 9 cm. to 10 cm. long.

*Petiole*—Medium caliper; from 8 mm. to 10 mm. long; shallow groove along upper surface; glabrous.

*Shape.*—Near oval. Apex—usually quite extended and acute. Base—usually somewhat acute. Margin with small, simple serrations except lower quarter toward base is usually entire.

*Upper surface.*—Glossy. Color: Mature leaves—between Dark Dull Yellow-Green, Plate XXXII (R) and Empire Green, Plate XXXII (R); young leaves—near Deep Dull Yellow-Green (1), Plate XXXII (R); veins lighter in color.

*Lower surface.*—Glossy. Color: Mature leaves—near Absinthe Green, Plate XXXI (R); young leaves—near Absinthe Green, Plate XXXI (R); veins darker in color.

*Flower*

Flowers borne: Sessile; terminal or axillary; mostly single, but sometimes double and terminal.

Quantity of bloom: Abundant.

Time of bloom: One season; usually from mid-February through April at Ontario, California.

Fragrance: None.

Bud:

*Size.*—Medium.

*Form.*—Usually ovoid.

*Sepals.*—Numerous (usually 8 or 9); increasing in size from the very small outermost to the much larger innermost sepals; between round and obovate in shape, with usually a single notch at apex; the one or two innermost sepals usually show transition to petals with streaks or a blush of red color like the petals. Outer surface—pubescent; color—near Chrysolite Green, Plate XXXI (R).

*Opening.*—Opens up well.

Bloom:

*Size (when fully open).*—From medium to large; averages from 9 cm. to 12 cm. in diameter.

*Petalage.*—Semi-double; usually from 14 to 16 petals; outermost petal is often reduced in size and is sometimes more a sepal than a petal.

*Form.*—Newly opening flower is cupped, with open center, while at maturity, the form is rather flat and open or rose form, with the petals lying rather flat together, and the margins of the petals rather wavy and gently reflexed outward in an informal manner, while an occasional inner petal is rather sharply folded and more upstanding than the others.

*Petals.*—Thickness — moderate. Surfaces — satiny, both inside and outside. Shape—somewhat irregular, but generally nearly round; usually one, but sometimes two notches at the apex, with an occasional notch elsewhere on the margin of some petals; point of attachment usually a definitely extended, though short, projection.

*Color.*—Newly opened flower: Outer petals—outside surface—near Currant Red Plate 821/3, page 167 (W), with veins slightly darker; inside surface—same as outside surface; inner petals—same as outer petals. 2–3 days open flower: Outer petals—outside surface—between Crimson, Plate 22/1, page 22 (W) and Currant Red, Plate 821/3, page 167 (W), with veins somewhat darker; inside surface—same as outside surface; inner petals —same as outer petals.

*General color effect.*—Newly opened flower—near Currant Red, Plate 821/3, page 167 (W). 2–3 days open flower—between Crimson, Plate 22/1, page 22 (W) and Currant Red, Plate 821/3, page 167 (W).

*Behavior.*—Flowers persist on plant until they become old and then drop off cleanly as one flower, since petals are usually united together at point of attachment.

*Longevity.*—On plant in garden—from 4 to 7 days in moderate weather. Cut flowers grown outdoors and kept at living room temperature—from 3 to 5 days.

*Reproductive organs*

Stamens: Usually from 90 to 100 in number; most with anthers. Length—commonly about 25 mm.

Filaments: Variably united in a cylinder, with the outermost united for approximately the first 9 or 10 mm. Color—from near Dawn Pink, Plate 523/3, page 137 (W) at base, to near Amber Yellow, Plate 505/3, page 132 (W) at top of filament.

Anthers: Color—general effect of near Buttercup Yellow, Plate 5/1, page 5 (W); no blackening with age.

Pistils: Three in number.

Styles: Separate. Length—from 8 to 10 mm.

Ovaries: Fused; pubescent. Color—near Chartreuse Green, Plate 663/3, page 90 (W).

Seed pods: None.

I claim:

A new and distinct variety of camellia plant, substantially as herein shown and described, characterized particularly as to novelty by the unique combination of a moderately vigorous, upright-spreading and bushy plant habit, attractive, medium-sized, dark green, leathery and glossy foliage, a precocious flowering habit, with the flowers blooming well while the plant is still quite small and young, as compared with other *C. japonica* varieties, and a very floriferous habit, with the flowers borne both terminally and laterally on the stems, attractive, semi-double flowers of graceful, irregular form, a distinctive, attractive and bright general color tonality of the flowers corresponding to near Currant Red, with a glowing quality that is characteristic of *C. japonica* and *C. saluenensis* hybrids, a mid-season to late blooming period, and a habit of all flowers dropping cleanly as one flower.

No references cited.

ABRAHAM G. STONE, *Primary Examiner.*

R. E. BAGWILL, *Assistant Examiner.*